United States Patent [19]
Laird et al.

[11] Patent Number: 5,677,765
[45] Date of Patent: Oct. 14, 1997

[54] METHOD FOR CALIBRATING A TOPOGRAPHIC INSTRUMENT

[75] Inventors: Ellen R. Laird, San Jose; W. Murray Bullis, Sunnyvale; James J. Greed, Jr., Los Gatos; Bradley W. Scheer, San Jose, all of Calif.

[73] Assignee: VLSI Standards, Inc., San Jose, Calif.

[21] Appl. No.: 698,959

[22] Filed: Aug. 16, 1996

Related U.S. Application Data

[62] Division of Ser. No. 539,973, Oct. 6, 1995, Pat. No. 5,599,464.

[51] Int. Cl.$^6$ ........................................ G01J 1/02
[52] U.S. Cl. ........................................ 356/243; 250/252.1
[58] Field of Search ........................................ 356/243, 237; 250/252.1

[56] References Cited

U.S. PATENT DOCUMENTS

| | | | |
|---|---|---|---|
| 4,386,850 | 6/1983 | Leahy | 356/243 |
| 4,597,665 | 7/1986 | Galbraith et al. | 356/237 |
| 4,615,762 | 10/1986 | Jastrzebski et al. | 156/628 |
| 5,169,488 | 12/1992 | Giuffre et al. | 156/643 |
| 5,198,869 | 3/1993 | Monteverde et al. | 356/243 |
| 5,332,470 | 7/1994 | Crotti | 156/659.1 |
| 5,383,018 | 1/1995 | Sadjadi | 356/243 |
| 5,520,769 | 5/1996 | Barrett et al. | 156/626.1 |

FOREIGN PATENT DOCUMENTS

| | | |
|---|---|---|
| 1-20428 A | 1/1989 | Japan . |
| 4-289411 | 10/1992 | Japan . |

OTHER PUBLICATIONS

M.L. Hitchman et al., "Calibration standards for surface profile monitors", *J. Phys. E: Sci. Instrum.*, vol. 13 (1), pp. 19–20 (1980).

T. Ohmi et al., "Calibration of height in atomic force microscope images with subnanometer scale silicon dioxide steps", *Appl. Phys. Lett.*, vol. 61 (20), pp. 2479–2481 (1992).

G. A. Candela et al., "Film thickness and refractive index Standard Reference Material calibration by ellipsometry and prolifometry", *SPIE* vol. 661 Optical Testing and Metrology, pp. 402–407 (1986).

*Primary Examiner*—Frank G. Font
*Assistant Examiner*—Amanda Merlino
*Attorney, Agent, or Firm*—Thomas Schneck; George B.F. Yee

[57] ABSTRACT

A method for calibrating topographic instruments, operating at sub-micrometer resolution levels, includes providing a calibration standard having a known one-dimensional power spectral density function. A roughness is calculated from the known one dimensional power spectral density function in relation to an atomic scale topographic dimension, $\Delta z_i$. The roughness of the calibration standard is measured by detecting light scattering therefrom and computing an isotropic power spectral density curve over the effective spatial bandwidth of the topographic instrument being calibrated. The measured roughness is then compared against the calculated roughness to determine whether the two values of roughness coincide.

15 Claims, 4 Drawing Sheets

METHOD FOR CALIBRATING A TOPOGRAPHIC INSTRUMENT

CROSS-REFERENCE TO RELATED APPLICATION

This is a divisional of patent application Ser. No. 08/539,973 filed on Oct. 6 1995, now U.S. Pat. No. 5,599,464.

TECHNICAL FIELD

The present invention relates to methods for making calibration standards used to determine surface roughness, texture and haze in instruments such as optical surface scanners, mechanical profilers and scanning probe microscopes.

BACKGROUND ART

Frequently in semiconductor manufacturing, the starting quality of incoming silicon material may have a profound effect on the final electrical device quality. A silicon wafer characteristic of interest is surface micro-roughness, sometimes called "haze", measured by a topographic inspection device, such as a surface scanner. Surface roughness is of interest in other industrial manufacturing processes, such as disk and optical component fabrication, particularly with increasing demands for quality control. Since topographic inspection instruments function at various spatial bandwidths, with varying response functions, it has been difficult to characterize these instruments since each may be reporting a very different value from the same surface. The range of spatial wavelengths observed by the instrument generally means the data sampling rate per unit distance. Sometimes the spatial bandwidth is expressed as spatial frequency and computed from the one dimensional grating equation:

$$f = \frac{\sin\theta_s - \sin\theta_i}{\lambda} \qquad \text{Eq. (1)}$$

where f is the spatial frequency, $\theta_i$ is the angle of incidence of a monochromatic light beam, $\theta_n$ is the principal scattering angle from the grating, and $\lambda$ is the wavelength of the beam. Alternatively, the ASTM has suggested a definition of spatial frequency in terms of a frequency range of a component of the Fourier transformed surface profile of an object. Calibration targets have been built to help obtain standard readings from some devices, particularly scanners. Such targets have been built to replicate haze patterns present on new, unpatterned, polished wafer surfaces.

The surface of a calibration target or standard should be extremely uniform and isotropic over a zone of interest, should be readily reproduced, and should have extremely small surface features to read the extremely low level values of haze which replicate the surface of prime silicon wafers. Such a haze standard was described by Scheer in U.S. Pat. No. 5,198,869, "Reference Wafer for Haze Calibration". The device described there however, envisions a haze standard that reads at a much higher level than would be useful for relating to a prime silicon wafer. The standard described was very useful but was comprised of two materials, one of which is a film layer causing additional effects from the optical path length differences through the film as well as phase shifts at the interfaces. Both of these effects will change with illumination wavelength and should therefore be eliminated. The reading device is a light collector of the type described in U.S. Pat. No. 4,597,665, assigned to Tencor Instruments, although other beam reading devices could be used. Various types of features have been used to simulate haze or roughness including pits, step height bars, line-space pairs and grid patterns. In most instances, these features were fabricated by photolithography on silicon substrates.

Calibration targets for another application of interest simulate a magnetic disk surface texture. Such targets must deal with a predominant mechanical effect that can reduce the reliability, or functionality, of disk recording media, referred to as stick-slip, or, in its worst manifestation, blocking. Stick-slip is due to a high coefficient of friction that causes irregularities in the rotational speed of rigid recording disks. Since the system is dependent on a steady rate of data from the recording medium, stick-slip invariably will result in loss of data integrity. Blocking, on the other hand, can cause the heads to adhere completely to the disk surface. A final phenomenon, related to blocking, is called stiction and may be described as occasional blocking. This again will lead to premature mechanical wear.

All three of these effects may occur if the surfaces of the recording head or the media surface are too finely polished. To avoid these problems, a defined amount of surface texture must be imparted onto the surfaces themselves. This is known in the prior art. The amount of this imparted surface texture must be carefully controlled because it is desired to have the head in the required close proximity to the recording surface. This texture may be modelled with a calibration target and observed by a surface topographic inspection instrument.

Consequently, there is a need for a calibration target which models the tribological properties of the head-disk interface, particularly the surface topography of the disk coating.

An object of the invention was to devise a calibration target which would replicate the microroughness of highly polished wafer or disk surfaces at the lower limits of step height resolution, i.e. atomic distances.

SUMMARY OF INVENTION

The above object is achieved with a single material silicon calibration target having surface texture with feature heights on the order of 8 Å to 100 Å, but preferably atomic scale, about 10 Å. Features having atomic scale vertical step heights are obtained by oxidation and etching of a silicon wafer. Oxygen atoms migrate into silicon, associating with silicon atoms of a substrate into silicon dioxide, allowing isolation of step heights having an atomic scale dimension. This is readily achieved with oxidation of silicon because an ambient reoxidation process is self-limiting at a given temperature, proceeding to a limited depth and then stopping. These atomic scale features are organized as arrays of pits or bars or a grid pattern, etc., in a major surface, typically planar, of the calibration target. Where pits have a random placement as described in U.S. Pat. No. 5,198,869, the calibration target is a haze standard.

The features may be formed in a thick oxide layer by first patterning the features, such as pits or stripes, using photoresist and a photomask. The areawise shape and distribution of the features is selected for mimicking the roughness of a test material to be scanned by a topographic measuring instrument. In one embodiment, the areas defined by the photomask pattern in the photoresist are etched into the thick oxide layer, so that the bare silicon is exposed in the etched areas. Next, a layer of thin oxide, e.g. native oxide, is formed in the etched areas when the bare silicon is exposed to an oxygen-rich environment. The silicon surface now contains shallow pits of atomic dimension in the previously patterned and etched areas. The height of these pits is only the distance to which the thin oxide extended into the substrate surface below the thick oxide. By clustering one million or more pits per square centimeter, with quasi-random placement, haze in wafer surfaces may be simulated for calibrating the lower limits of vertical resolution of an optical scanner.

Since the etched pits may be precisely located in known x-y coordinates as taught in U.S. Pat. No. 5,198,869, it is possible to replicate a given level of RMS roughness on a wafer's surface. The total etched area, combined with the etch depth, give roughness levels which are easily predicted mathematically. The derivation of this simple equation simply relates the etch depth, $\Delta z$, to the etched pit diameter, $d_p$, and the area of the scan, $A_{scan}$. If there is only one etched pit size, $A_{scan}$ is equal to the imaginary boxed area surrounding the pit. For n pit sizes, $(d_p=d_{p1}, d_{p2}, \ldots, d_{pn})$ multiply n times $A_{scan}$ according to the following:

$$R_q = \Delta Z \left[ \frac{\pi}{4nA_{scan}} \sum_{i=1}^{n} d_{pi}^2 \right]^{1/2} \quad \text{Eq. (2)}$$

When using a single sized circular pit, a phenomenon known as Airy disk diffraction occurs when the pits are detected. This has the effect of producing pronounced dips in the PSD curve. Since the pit diameter is directly related to the Airy disk minima in the PSD curve, it is possible to directly find the pit diameters simply by relating the one-dimensional grating equation to the Airy disk equation. The utility of this is realized by including the area of this pit ($\pi d_p^2/4$) into the derived equation above. Since the scan area is known, the value of $\Delta z$, a very small step height, can be backed out directly. This is very useful for the calibration of very small vertical distances on atomic force microscopes.

However, this same phenomenon can be an interference when using this artifact to calibrate haze on a wafer scanning system. If the spatial bandwidth boundary of the scanner coincides with one of these minima, an additional uncertainty is added in the determination of haze. However, this can be dealt with directly in one of several ways: 1) by placing two pit diameters on the wafer's surface, alternating the two, one each in each adjoining "box", where the diameters are related by the multiples of the zeroth and first order Bessel functions (as contained in the Airy disk equation), then their resulting minima and maxima would overlap, thus smoothing out the PSD curve; 2) by using random sizes of pits within a given size range, the collective effect would also smooth out the PSD curve; and finally, 3) by etching these random pit sizes in close proximity, say three to a "box", each placed by a random vector which has a magnitude equal to the radius of the pit in that particular box, with the vector tail placed at the center of the initial pit placed in the box, then the final shape would not be circular, also eliminating any diffraction pattern. Each "box" is an imaginary section or grid square on the surface of a wafer as described in U.S. Pat. No. 5,198,869. Using the described technique, the etched areas have atomic scale vertical step heights, making it possible to characterize instruments such as atomic force microscopes, optical profilers, scanners and the like.

BEST MODE FOR CARRYING OUT THE INVENTION

Figure 1:
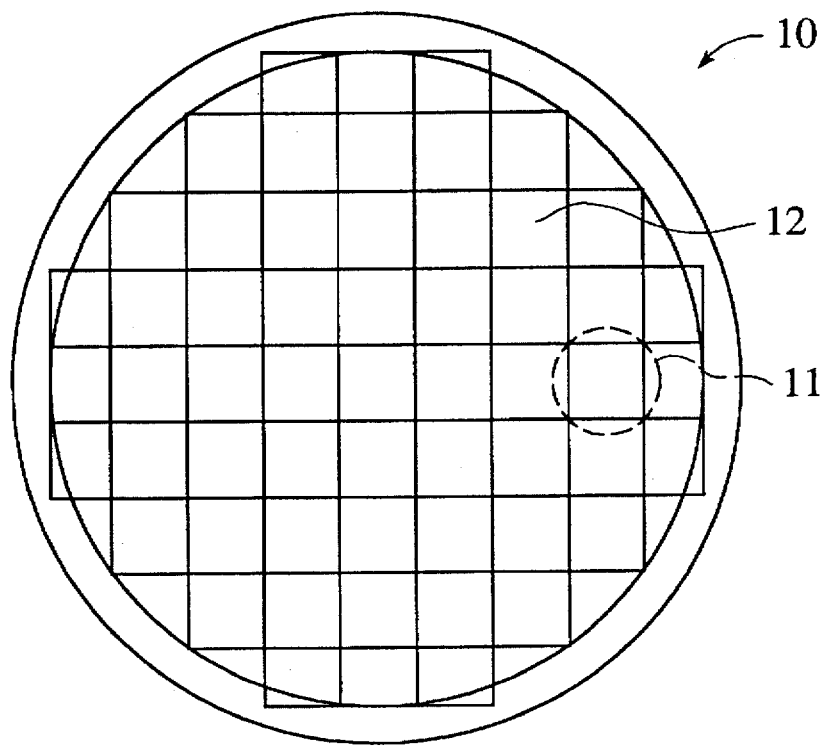
FIG. 1 is a top plan view of a calibration target in accord with the present invention.

With reference to FIG. 1, a silicon wafer 10 is shown divided into a plurality of imaginary sections 12. The wafer is a highly polished semiconductor substrate, i.e. a bare polished wafer. The sections 12 are not physically marked on the wafer and do not extend all the way to the edge of the wafer. The sections 12 are for the purpose of indicating that selected sections, such as a checkerboard pattern, could be used to contain features of the present invention. Alternatively, the entire surface may be covered with the features, which are designed to mimic the effect of haze on a highly polished wafer surface.

Figure 2:
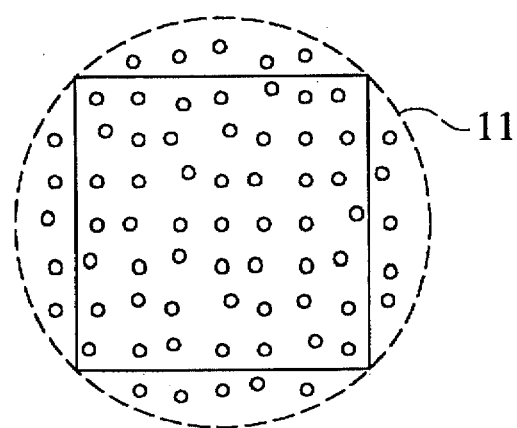
FIG. 2 is a magnification of a small portion of the calibration target of FIG. 1.

In FIG. 2, an enlargement of zone 11 of wafer 10 in FIG. 1 with the features placed in a quasi-random distribution, as indicated in U.S. Pat. No. 5,198,869 to simulate haze. For purposes of illustration, the density of features has been greatly reduced. The difference between the features described herein and the features described in U.S. Pat. No. 5,198,869 is that the features of the present invention have atomic scale step height or depth, on the order of about 10 Å, with a density of more than one million features per square centimeter. Placement of the features should be such that no interference pattern is formed by light scattered by the pattern in the presence of incident illumination.

Figure 3:
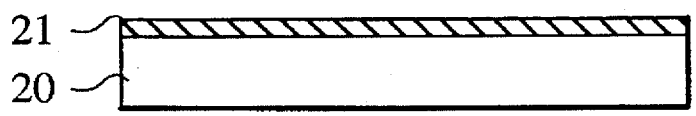
FIGS. 3–8 are side views of a microscopic portion of a calibration target, showing sectional views of a formation of a single feature in accord with the present invention.

In FIGS. 3–8, manufacture of a single feature is shown, but in practice, all of the features on the wafer, perhaps millions, would be made simultaneously. FIG. 3 shows a silicon wafer 20 having a uniform layer 21 of silicon dioxide thermally grown onto the silicon substrate. The silicon dioxide layer has a thickness of between 500 Å and 1000 Å. In the book *Silicon Processing for the VLSI Era*, vol. 1, p. 200–212, the thermal oxidation of silicon is explained. The book mentions that Deal and Grove described silicon oxidation as proceeding by the diffusion of an oxidant, such as molecular oxygen, through an existing oxide to the silicon-silicon dioxide interface, where molecules react with silicon to form silicon dioxide. In other words, oxygen migrates to the bare silicon substrate, where it interacts with silicon, thereby lowering the level of the silicon/silicon dioxide interface in places where oxidation has occurred. This is a key aspect of the present invention.

Figure 4:
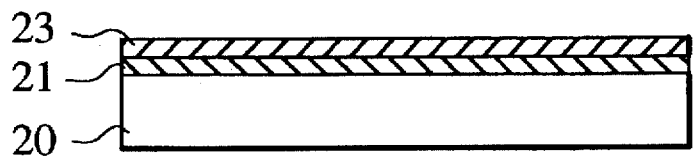

In FIG. 4, a thin layer 23 of positive photoresist is applied. The photoresist may be patterned with the desired location, areawise extent and overall density of features by means of a mask. When light is used to expose the photoresist layer 23 through the mask, a latent image of the features is formed in the photoresist by light. In other words, the chemical bonds in the exposed photoresist are broken, altering the molecular weight and solubility of the resist, which allows the latent image to be developed, removing the exposed photoresist in the etched area, uncovering the underlying silicon dioxide layer. In the case of positive photoresist, the bonds of the exposed photoresist are broken.

Figure 5:
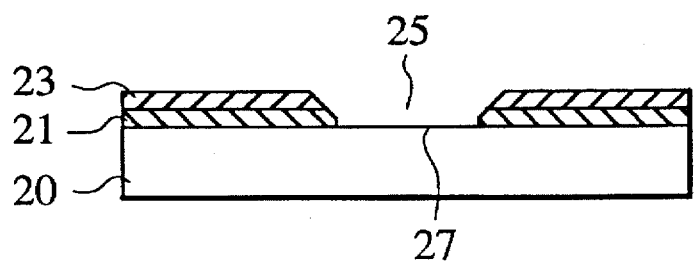

In FIG. 5, portions of the resist layer 23, now removed, create an aperture 25 where the resist has been exposed by light. An oxide etchant is used to remove silicon dioxide down to the upper surface 27 of the silicon substrate 20, which is uniformly lower than the original level.

Figure 6:
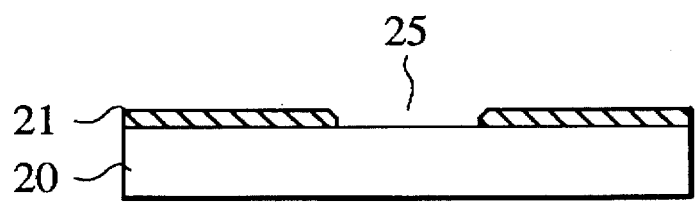
Figure 7:
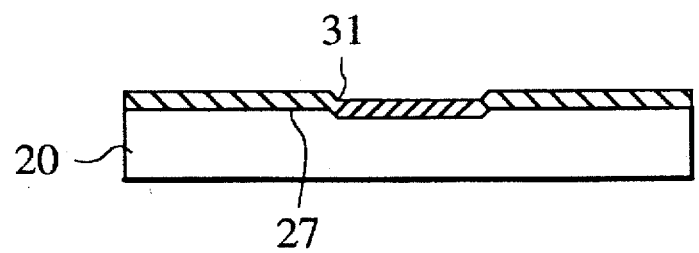

In FIG. 6, the photoresist is stripped from the oxide layer 21. The aperture region 25, now a single pit 31 in an array of similar pits which will form topographic features, including the light scattering features of the present invention, undergo self-limiting reoxidation due to exposure to air. Any oxidizing ambient environment could be used, but air is effective and inexpensive. Air oxidation at room temperature produces native oxide which has a thickness of approximately 17 Å. Approximately half of the native oxide layer consumes silicon at the substrate interface. This is shown in FIG. 7, where the native oxide at the bottom of a pit extends into the silicon substrate, below the former level 27 supporting the silicon dioxide. The formation of the native oxide layer is rapid, but generally stops by itself after a short time.

Figure 8:
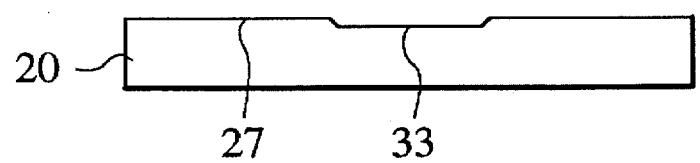

Next, all of the oxide is stripped, as shown in FIG. 8. It is now apparent that a differential step height exists between the bottom of the pit 33 and the former base 27 which supported the silicon dioxide.

In FIGS. 3-8, the construction of a topographic feature has been shown using a dark field mask, resulting in a pit within a light reflecting field. A reverse process could be used, producing a feature having a step height, rather than a pit. The reverse process could be achieved with reverse masks or with photoresist of the opposite type.

Figure 9:
FIGS. 9–14 are side views of a microscopic portion of a calibration target, showing sectional views of an alternative formation method.

In FIG. 9, a uniform thermal oxide layer 41 is grown on a polished, light-reflective silicon wafer to a thickness which is between 700 Å and 1000 Å. Such layers are readily produced in the semiconductor industry with good consistency and uniform thickness over the surface of a wafer. Lesser thicknesses could be produced, but the range of 700 Å to 1000 Å is preferred because of the ease of manufacturing and of verifying the thickness with measuring instruments.

Figure 10:
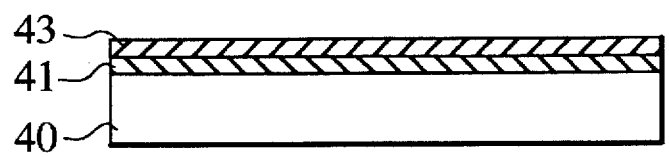

In FIG. 10, a layer of photoresist 43 is disposed over the thermal oxide layer 41. The photoresist is exposed to light through a mask which is the optical complement of the mask used for the exposure previously described with respect to FIGS. 4 and 5.

Figure 11:
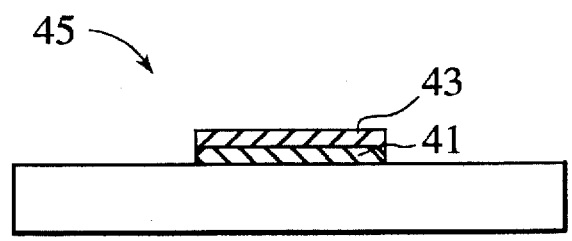
Figure 12:
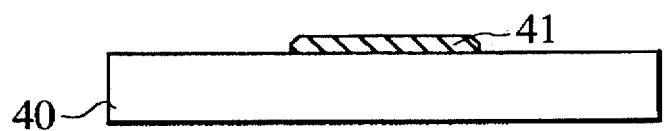

After removing the exposed portions of the photoresist and etching the oxide, a mesa is left, as shown in FIG. 11. The mesa 45 consists of a small layer of photoresist 43 atop a similarly sized layer of thermal oxide 41. In FIG. 12, the photoresist portion is shown to be stripped away.

Figure 13:
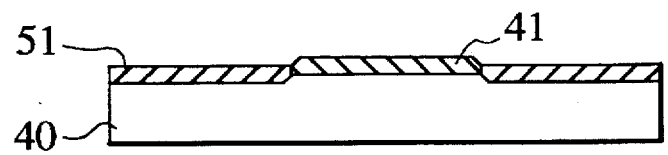
Figure 14:
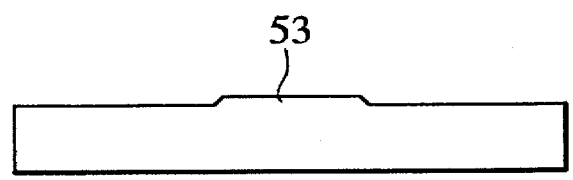

In FIG. 13, a very thin layer of native oxide 51 grows on the exposed silicon as air is allowed to be in contact with the wafer, consuming silicon below the initial wafer level. The silicon dioxide island 41 is removed, leaving a small mesa or feature 53, which also is exposed to air and has a uniformly thin native oxide layer. The feature 53 extends approximately 8 Å to 9 Å above the surface of surrounding silicon.

Laser scanners have a spatial resolution of approximately 50 micrometers. It is preferable to space the features described herein at approximately 1/10 this distance or every 5 microns. With a 100 µm typical beam diameter employed in a laser scanner, this means that approximately 300 pits are being illuminated at any given time. Therefore, it is not possible for the scanner to detect individual scattering features.

Figure 15:
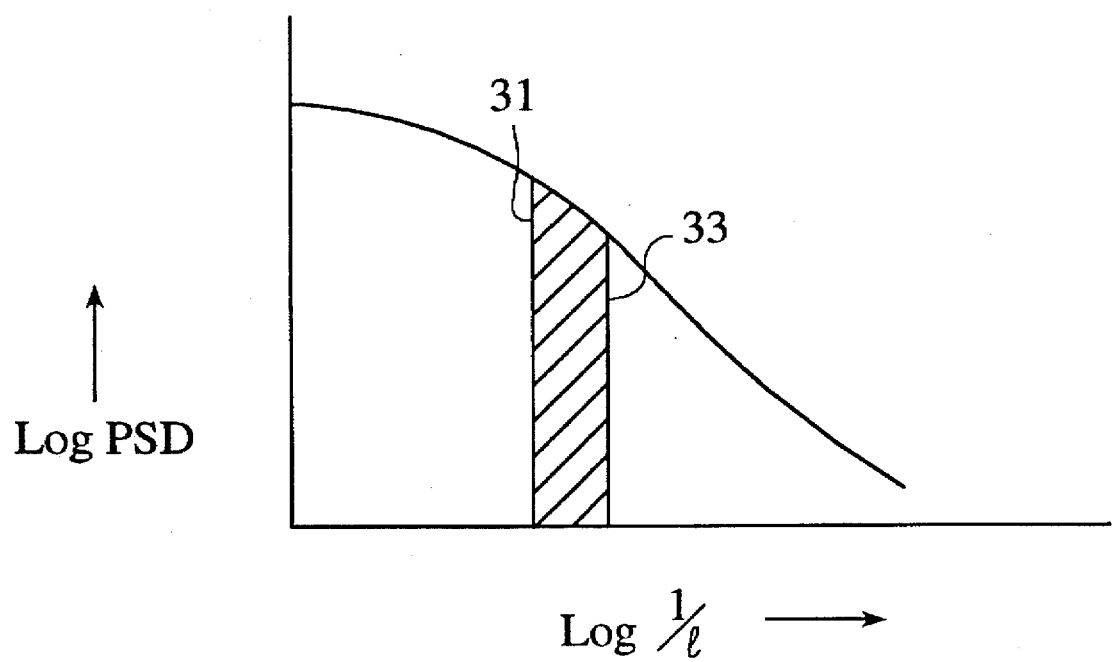
FIG. 15 is a graph depicting a one dimensional power spectral density curve of the isotropic calibration target shown in FIG. 1.

In calibrating a test instrument, the one-dimensional power spectral density curve for an isotropic calibration target is plotted. In FIG. 15, the logarithm of power spectral density (PSD), a quantity related to the amplitude of the detected light scattered or topographic amplitude detected from the feature, is plotted on the y-axis, while the spatial frequency 1/l, with l being spatial wavelength, is plotted along the x-axis (typically in inverse microns). The spatial wavelength l is the measure of the distance between surface peaks and valleys. For a given instrument, computed rms roughness, $R_{Q1}$, is defined as follows:

$$R_{Q1} = \sqrt{\int_{f_1}^{f_2} PSD(f) df} \qquad \text{Eq. (3)}$$

where $f_1$ and $f_2$ are the frequency limits of effective spatial bandwidth for that instrument, indicated by vertical lines 31 and 33 in FIG. 15, for a particular measuring instrument, and PSD is the power spectral density function. The shaded area under the curve is the square of the computed roughness value $R_{Q1}$. This value is defined in relation to $\Delta Z_i$, the variation from the mean surface level.

Different instruments will show different measured values of RMS roughness, $R_{QM}$, for the same calibration target, depending on the spatial bandwidth and response function of the instrument. The RMS roughness of a particular calibration standard, having a particular value of $\Delta Z_i$ chosen to obtain a value $R_q$ in the range of interest, becomes known as $R_{Q1}$ for a particular set of values for $f_1$ and $f_2$. For a particular instrument under test, $f_1$ and $f_2$ may be tested or determined readily from instrument attributes. If the instrument operates satisfactorily between $f_1$ and $f_2$ while testing the calibration target, and the measured $R_{QM}$ generally corresponds to the value $R_{Q1}$ calculated using equation (3), then the instrument is properly calibrated for detection of either a given microroughness value or a given haze level. Different targets, each with a different $\Delta Z_i$, may be used to establish the sensitivity of the instrument.

It is noted that methods for measuring surface roughness are known to those of ordinary skill in the relevant arts. Similarly, the power spectral density function of an instrument is readily determined.

We claim:

1. A method for calibrating an instrument for measuring atomic scale vertical topographic dimensions comprising, establishing the spatial frequency limits, $f_1$ and $f_2$, of the effective spatial bandwidth for said instrument, providing a calibration standard having an atomic scale vertical topographic dimension, $\Delta Z_i$, and a determined PSD (power spectral density) function over spatial frequency limits greater than those of said instrument, measuring an RMS roughness, $R_{QM}$, of the calibration standard with said instrument, defining a measured roughness, integrating the isotropic power spectral density curve between the limits $f_1$ and $f_2$ to determine computed RMS roughness, $R_{Q1}$, and comparing the measured roughness, $R_{QM}$, and the computed roughness $R_{Q1}$ for one or more vertical topographic dimensions, $\Delta Z_i$.

2. The method of claim 1 wherein said comparing step includes plotting an isotropic one-dimensional power spectral density curve corresponding to said measured roughness.

3. A method for calibrating an instrument for measuring atomic scale vertical topographic dimensions comprising the steps of:

providing a calibration standard having a known roughness and a known power spectral density function associated with said known roughness;

measuring, with said instrument, a roughness of said calibration standard as a function of a measured power spectral density function, defining a measured roughness; and comparing said known roughness with said measured roughness.

4. The method as recited in claim 3 wherein said known roughness is associated with a known spatial frequency range that corresponds to an effective spatial bandwidth for said instrument and said measuring step includes measuring said measured power spectral density function over said known range.

5. The method as recited in claim 3 wherein said comparing step includes plotting a one-dimensional power spectral density curve which corresponds to said measured roughness.

6. The method as recited in claim 3 wherein said measured roughness is defined as a function of an atomic scale vertical topographic dimension $\Delta z_i$.

7. The method as recited in claim 3 wherein said calibration standard has an etched surface and said known roughness is determined as a function of both a total area of said etched surface and a depth of said etched area.

8. The method as recited in claim 3 wherein said known roughness is calculated by integrating said known power spectral density function over said known spatial frequency range.

9. The method as recited in claim 3 wherein said measured roughness is determined by integrating said measured power spectral density function over said known spatial frequency range.

10. The method as recited in claim 3 wherein said measuring step includes detecting light scattered from said calibration standard.

11. A method for calibrating an instrument for measuring atomic scale vertical topographic dimensions comprising the steps of:

providing a calibration standard having an atomic scale vertical topographic dimension, $\Delta z_i$, over an area $A_i$;

calculating a roughness of said calibration standard as a function of a known isotropic power spectral density function, defining a calculated roughness;

measuring, with said instrument, a roughness of said calibration standard, defining a measured roughness; and comparing said calculated roughness with said measured roughness.

12. The method of claim 11 wherein said measuring step includes integrating a measured isotropic power spectral density function over a predetermined spatial frequency range.

13. The method of claim 12 wherein said predetermined spatial frequency ranges envelops an effective spatial bandwidth for said instrument.

14. The method of claim 13 wherein said comparing step includes plotting a one-dimensional power spectral density curve which corresponds to said measured roughness.

15. The method of claim 14 wherein both said known power spectral density function and said measured power spectral density function are each determined as a function of said area $A_i$ and said vertical topographic dimension, $\Delta z_i$.

* * * * *